United States Patent
Kim et al.

(10) Patent No.: US 8,075,923 B2
(45) Date of Patent: *Dec. 13, 2011

(54) USE OF HEDERAGENIN 3-O-α-L-RHAMNOPYRANOSYL(1→2)-(β-D-GLUCOPYRANOSYL(1→4)-α-L-ARABINOPYRANOSIDE OR AN EXTRACT FROM PULSATILLAE RADIX CONTAINING THE SAME AS A THERAPEUTIC AGENT FOR SOLID TUMORS

(75) Inventors: Song-Bae Kim, Gongju-Shi (KR);
Byung-Zun Ahn, Yousung-Gu (KR);
Yong Kim, Joong-Gu (KR)

(73) Assignee: Song-Bae Kim, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 12/709,907

(22) Filed: Feb. 22, 2010

(65) Prior Publication Data

US 2010/0152124 A1    Jun. 17, 2010

Related U.S. Application Data

(63) Continuation of application No. 11/107,665, filed on Apr. 15, 2005, now Pat. No. 7,682,638, which is a continuation-in-part of application No. 10/620,709, filed on Jul. 15, 2003, now abandoned.

(30) Foreign Application Priority Data

Jul. 22, 2002 (KR) .................. 2002-43016

(51) Int. Cl.
*A61K 36/00* (2006.01)

(52) U.S. Cl. ....................................... 424/723; 424/725
(58) Field of Classification Search .................. None
See application file for complete search history.

(56) References Cited

U.S. PATENT DOCUMENTS

| 3,351,582 A | 11/1967 | Balansard et al. |
| 5,595,756 A | 1/1997 | Bally et al. |
| 5,980,870 A | 11/1999 | Baik et al. |
| 6,071,521 A | 6/2000 | Kim |

FOREIGN PATENT DOCUMENTS

KR     10-0315200     3/2002

OTHER PUBLICATIONS

Bae, "Korean Medicinal Herbs" (1999).
Shimizu et al., "Chem. Pharm. Bull.", vol. 26, pp. 1666-1671 (1978).

(Continued)

*Primary Examiner* — Patricia Leith
(74) *Attorney, Agent, or Firm* — Peter F. Corless; Christine C. O'Day; Edwards Wildman Palmer LLP

(57) ABSTRACT

This invention relates to a use of hederagenin 3-O-α-L-rhamnopyranosyl((1→2)-[β-D-glucopyranosyl(1→4)]-α-L-arabinopyranoside or a Pulsatillae radix extract containing the same as a therapeutic agent for solid tumors. Also, this invention relates to a method of preparing a therapeutic agent for solid tumors by using hederagenin 3-0-α-L-rhamnopyranosyl(1→2)-[β-D-glucopyranosyl(1→4)]-α-L-arabinopyranoside, or a method of treating a subject suffering from solid tumors, comprising administering to the subject a therapeutically effective dose of hederagenin 3-0-α-L-rhamnopyranosyl(1→2)-[β-D-glucopyranosyl(1→4)]-α-L-arabinopyranoside.

6 Claims, 3 Drawing Sheets

OTHER PUBLICATIONS

Yoshihiro et al., "Journ. Nat. Prod.", vol. 62, pp. 1279-1283 (1999).
Ekabo et al., "Journ. Nat. Prod.", vol. 59, pp. 431-435 (1996).
Kang, "Arch. Pharm. Res.", vol. 12(1), pp. 42-47 (1989).
HB MacPhillamy et al., *Plant Science Bulletin*, 9(2), pp. 1-15 (Apr. 1963)—printed from the internet.
J. Phillipson et al., "New Drugs from Nature—It Could be Yew", *Phytotherapy Research 13*, pp. 2-8 (1999).
Raskin et al., "Can An Apple a Day Keep the Doctor Away?", *Current Pharmaceutical Design*, vol. 10, pp. 3419-3429 (2004).
Ravilla et al., "Comparison of Several Procedures Used for the Extraction of Anthocynains from Red Grapes", *J. Agric. Food Chem.*, vol. 46, pp. 4592-4597 (1998).
Wikipedia: Pasque Flower; Wikipedia Online, URL<http://en.wikipedia.org/wiki/Pasque_flower>, pp. 1-3, accessed Jun. 16, 2009.
Barthomeuf et al., "In Vitro Activity of Hederacolchisid A1 Compared with Saponins from *Hedera colchica* Against Proliferation of Human Carcinoma and Melanoma Cells", *Planta Medica*, vol. 68, pp. 672-675 (Aug. 2002).
T. Gura et al., "Systems for Identifying New Drugs are Often Faulty", *Science*, vol. 278, pp. 1041-1042 (Nov. 1997).
Chabner et al., "Chemotherapy and the War on Cancer", *Nature Reviews*, vol. 5, pp. 65-72 (Jan. 2005).
Mimaki et al., "Triterpene Saponins and Lignans from the Roots of *Pulsatilla chinensis* and Their Cytotoxic Activity Against HL-60 Cells", *J. Nat. Prod.*, vol. 62, pp. 1279-1283 (1999).

ACETONE FRACTION1
EXTRACT

USE OF HEDERAGENIN 3-O-α-L-RHAMNOPYRANOSYL(1→2)-(β-D-GLUCOPYRANOSYL(1→4)-α-L-ARABINOPYRANOSIDE OR AN EXTRACT FROM PULSATILLAE RADIX CONTAINING THE SAME AS A THERAPEUTIC AGENT FOR SOLID TUMORS

This application is a continuation of U.S. patent application Ser. No. 11/107,665, filed on Apr. 15, 2005, which in turn was a continuation-in-part of U.S. patent application Ser. No. 10/620,709, filed on Jul. 15, 2003.

TECHNICAL FIELD

This invention relates to a use of hederagenin 3-O-α-L-rhamnopyranosyl ((1→2)-[β-D-glucopyranosyl(1→4)]-α-L-arabinopyranoside as represented by the following formula (I):

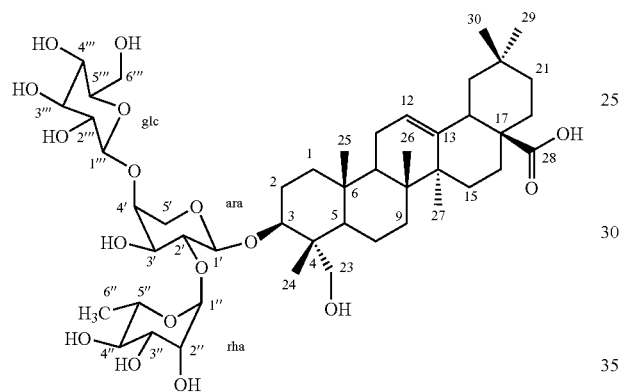

or a water-soluble fraction of Pulsatillae radix containing the same as a therapeutic agent for solid tumors.

Also, this invention relates to a method of preparing a therapeutic agent for solid tumors by using hederagenin 3-O-α-L-rhamnopyranosyl(1→2)-[β-D-glucopyranosyl (1→4)]-α-L-arabinopyranoside, and to a method of treating a subject suffering from solid tumors, comprising administering to the subject a therapeutically effective dose of hederagenin 3-O-α-L-rhamnopyranosyl(1→2)-[β-D-glucopyranosyl (1→4)]-α-L-arabinopyranoside.

BACKGROUND ART

Pulsatillae radix is a dried root of *Pulsatilla* species belonging to the Ranunculaceae family (Ki Hwan Bae, Korean Medicinal Herbs, 1999). According to the Chinese medicine, Pulsatillae radix is known to have effects of removing heat from the blood and detoxifying. It has also been used as anti-inflammatory, astringent, hemostatic and antidiarrhea agents, and for the treatment of hematochezia, malaria, nosebleed, and bleeding from tooth. Its flower is called as Pulsatillae Flos, and used for the treatment of malaria, or smallpox. Its leaf is called as Pulsatillae Folium, and used for treatment of waist pain, edema, or heart pain. In addition, decoction of Pulsatillae radix was reported to have an antibacterial effect against amoebic dysentery, and a pesticidal effect against Trichomonas.

Pulsatillae radix contains about 9% of saponins, and such ingredients as protoanemonin, anemonin, ranunculin, hederagenin, betulinic acid, and oleanolic acid derivatives and their glycosides have been isolated therefrom by now as represented by the following formula (II):

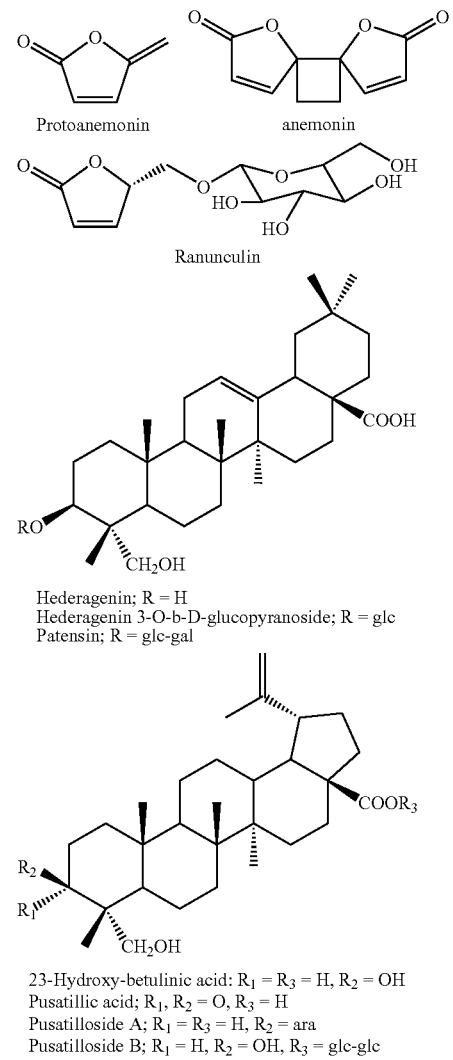

The above ingredients have not yet been extensively studied for their pharmacological effects, but protoanemonin was reported to have mitotoxicity (Vonderbank, F., *Pharmazie* 5, 210, 1950). Li, et al. (Li, R. Z., et al., *Yao Hsueh Hsueh Pao.* 28, 326 31, 1993) also reported that ranunculin has cytotoxicity against KB cells, by inhibition of DNA polymerase.

Hederagenin 3-O-α-L-rhamnopyranosyl(1→2)-[β-D-glucopyranosyl(1→4)]-α-L-arabinopyranoside was isolated from *Pulsatilla cerna* and *P. koreana* by Shimizu, et al. (*Chem. Pharm. Bull.*, 26, 1666, 1978); from *P. chinensis* by Yoshihiro, et al. (*J. Nat. Pro.*, 62, 1279, 1999); and from *Serjania salzmanniana* Schlecht by Ekabo, et al. (J. Nat. Prod., 59, 431, 1996). Kang, et al. (*Arch. Pharm. Res.*, 12(1), 42-47, 1989) also isolated it from *P. koreana*, and reconfirmed its structure. Yoshihiro, et al. reported that hederagenin and oleanolic acid derivatives showed cytotoxicity against HL-60 human leukemia cells in the above article. They reported that hederagenin 3-O-α-L-rhamnopyranosyl(1→2)-[β-D-glucopyranosyl (1→4)]-α-L-arabinopyranoside isolated from Chinese Pulsatillae radix (*Pulsatilla chinensis*) had week cytotoxicity, i.e. 3.8 μg/ml of $ED_{50}$, against HL-60 cells.

However, most of saponins and many kinds of natural products commonly show such level of cytotoxicity, and thus, the above compound cannot be said to have antitumor activity based thereon. Therefore, it has never been known that hederagenin 3-O-α-L-rhamnopyranosyl (1→2)-[β-D-glucopyranosyl(1→4)]-α-L-arabinopyranoside has antitumor activity, particularly, against solid tumors.

DISCLOSURE OF THE INVENTION

The present inventors isolated deoxypodophyllotoxin from medicinal herbs including *Anthriscus sylvestris* Hoffman, Pulsatillae radix, etc., and found that this substance inhibited the growth of solid tumor cells by inhibiting angiogenesis, and obtained a Korean patent (Korean Patent Number 315, 200) for the same. The present inventors carried out extensive studies to develop an antitumor agent from medicinal herbs. As a result, they obtained a fraction which is poorly soluble in an organic solvent, but is readily soluble in water from Pulsatillae radix, and isolated an antitumor compound from the fraction, and so completed the present invention.

Accordingly, the purpose of the present invention is to provide a therapeutic agent for solid tumors comprising an antitumor compound isolated from Pulsatillae radix (hederagenin 3-O-α-L-rhamnopyranosyl(1→2)-[β-D-glucopyranosyl(1→4)]-α-L-arabinopyranoside) or a water-soluble fraction of Pulsatillae radix containing the same as an active ingredient, a method of preparing a therapeutic agent for solid tumors by using hederagenin 3-O-α-L-rhamnopyranosyl (1→2)-[β-D-glucopyranosyl(1→4)]-α-L-arabinopyranoside, or a method of treating a subject suffering from solid tumors, comprising administering to the subject a therapeutically effective dose of hederagenin 3-O-α-L-rhamnopyranosyl(1→2)-[β-D-glucopyranosyl(1→4)]-α-L-arabinopyranoside.

One aspect of the present invention provides a therapeutic agent for solid tumors comprising hederagenin 3-O-α-L-rhamnopyranosyl(1→2)-[β-D-glucopyranosyl(1→4)]-α-L-arabinopyranoside as an active ingredient.

Another aspect of the present invention provides a therapeutic agent for solid tumors comprising hederagenin 3-O-α-L-rhamnopyranosyl(1→2)-[β-D-glucopyranosyl (1→4)]-α-L-arabinopyranoside as an active ingredient, wherein said hederagenin 3-O-α-L-rhamnopyranosyl(1→2)-[β-D-glucopyranosyl(1→4)]-α-L-arabinopyranoside is contained in a water-soluble fraction of Pulsatillae radix obtained by extracting Pulsatillae radix with an aqueous solution of ethanol, and forming precipitates by adding acetone thereto.

Another aspect of the present invention provides a method of preparing a therapeutic agent for solid tumors by using hederagenin 3-O-α-L-rhamnopyranosyl(1→2) -[β-D-glucopyranosyl(1→4)]-α-L-arabinopyranoside.

Another aspect of the present invention provides a method of preparing a therapeutic agent for solid tumors by using hederagenin 3-O-α-L-rhamnopyranosyl(1→2) -[β-D-glucopyranosyl(1→4)]-α-L-arabinopyranoside, wherein said hederagenin 3-O-α-L-rhamnopyranosyl (1→2)-[β-D-glucopyranosyl(1→4)]-α-L-arabinopyranoside is contained in a water-soluble fraction of Pulsatillae radix obtained by extracting Pulsatillae radix with an aqueous solution of ethanol, and forming precipitates by adding acetone thereto.

Preferably, the water-soluble fraction of Pulsatillae radix is a fraction having $R_f$ in the range of 0.48 to 0.50, and developing red color and then blue color, upon spraying sulfuric acid followed by heating, wherein the water-soluble fraction of Pulsatillae radix is prepared by extracting Pulsatillae radix with an aqueous solution of ethanol, forming precipitates by adding acetone thereto to obtain a water-soluble fraction, and passing the fraction through a Sephadex LH20 column.

Another aspect of the present invention provides a method of treating a subject suffering from solid tumors, comprising administering to the subject a therapeutically effective dose of hederagenin 3-O-α-L-rhamnopyranosyl(1→2)-[β-D-glucopyranosyl (1→4)]-α-L-arabinopyranoside.

Another aspect of the present invention provides a method of treating a subject suffering from solid tumors, comprising administering to the subject a therapeutically effective dose of hederagenin 3-O-α-L-rhamnopyranosyl(1→2)-[β-D-glucopyranosyl(1→4)]-α-L-arabinopyranoside, wherein said hederagenin 3-O-α-L-rhamnopyranosyl(1→2)-[β-D-glucopyranosyl(1→4)]-α-L-arabinopyranoside is contained in a water-soluble fraction of Pulsatillae radix obtained by extracting Pulsatillae radix with an aqueous solution of ethanol, and forming precipitates by adding acetone thereto.

Preferably, the water-soluble fraction of Pulsatillae radix is a fraction having $R_f$ in the range of 0.48 to 0.50 and developing red color and then blue color, upon spraying sulfuric acid followed by heating, wherein the water-soluble fraction of Pulsatillae radix is prepared by extracting Pulsatillae radix with an aqueous solution of ethanol, forming precipitates by adding acetone thereto to obtain a water-soluble fraction, and passing the fraction through a Sephadex LH20 column.

"Solid tumors," as used herein, refer to any mass tumor except blood cancers, a representative example of which is lung tumor.

In the present invention, the Pulsatillae radix extract containing hederagenin 3-O-α-L-rhamnopyranosyl(1→2)-[β-D-glucopyranosyl(1→4)]-α-L-arabinopyranoside can be obtained by extracting Pulsatillae radix with an aqueous solution of ethanol, and forming precipitates by adding acetone thereto to obtain a water-soluble fraction (WT). Or, it can be obtained by extracting Pulsatillae radix with the aqueous solution of ethanol, forming precipitates by adding acetone thereto to obtain the water-soluble fraction, and passing the fraction through Sephadex LH20 column to obtain a fraction (SPX3) having $R_f$ of 0.48~0.5, and developing red color, and then, blue color upon spraying sulfuric acid followed by heating.

Hereinafter, the present invention will be explained in detail.

According to the present invention, Pulsatillae radix extract is extracted with 50% ethanol to obtain a fraction WT poorly soluble in acetone, and the fraction is further purified on Sephadex LH20 to obtain fraction SPX3, and from the SPX3 fraction, pure SB365 is finally obtained. This compound is hederagenin 3-O-α-L-rhamnopyranosyl (1→2)-[β-D-glucopyranosyl(1→4)]-α-L-arabinopyranoside, and exhibits higher antitumor activity against solid tumors formed with mouse lung tumor cells, LLC (Lewis Lung Carcinoma) cells, or human lung tumor cells, NCI-H23 cells, than a clinical drug, adriamycin.

The water-soluble fraction of Pulsatillae radix according to the method of the present invention is extracted with 50% ethanol, and acetone is added to the ethanol extract to remove acetone-dissolved part, and so the resulting water-soluble fraction of Pulsatillae radix comprises high concentration of hederagenin 3-O-α-L-rhamnopyranosyl (1→2)-[β-D-glucopyranosyl(1→4)]-α-L-arabinopyranoside.

According to an experiment for the content of hederagenin 3-O-α-L-rhamnopyranosyl (1→2)-[β-D-glucopyranosyl (1→4)]-α-L-arabinopyranoside, the water-soluble fraction of Pulsatillae radix according to the method of the present invention contains an average of 1.20 mg of hederagenin 3-O-α-L-rhamnopyranosyl(1→2)-[β-D-glucopyranosyl (1→4)]-α-L-arabinopyranoside per g. Therefore, the water-soluble fraction of Pulsatillae radix according to the method of the present invention provides superior antitumor activity against solid tumors.

In particular, the present process for preparing an antitumor fraction from Pulsatillae radix and isolating an antitumor substance therefrom is as follows.

(1) Preparation of Antitumor Fraction Wt from Pulsatillae Radix

Pulsatillae radix powder was extracted with 50% aqueous solution of ethanol, and dried under reduced pressure. To the obtained dried material was added acetone at 5 to 10-fold amount. The mixture was shaken, centrifuged at 3,000 rpm, and the supernatant was decanted therefrom to obtain an insoluble part. The above process was repeated twice. The remaining insoluble part was readily soluble in water, and so designated as "fraction WT." This fraction showed relatively high antitumor activity against BDF1 mice transplanted with LLC cells and nude mice transplanted with NCI-H23 cells.

(2) Preparation of Fraction Spx3 from Fraction Wt

A given amount of fraction WT is dissolved in a given amount of aqueous solution of methanol at various concentrations, and then fractionated on Sephadex LH20 column stabilized with the same solvent. In this case, the best isolation is achieved with employing 80% aqueous solution of methanol, and the suitable size of the filled column was 60×4 cm for 500 mg of fraction WT. As a result, fraction SPX1 (test tube numbers 26-66), SPX2 (test tube numbers 66-91), SPX3 (test tube numbers 91-111), and SPX4 (test tube numbers 111-138) were obtained. When spraying sulfuric acid onto the fractions developed on a silica gel plate and heating the plate, the fraction SPX3 developed red color at first, and blue color with the lapse of time, and contains a spotted compound having $R_f$ of 0.48 to 0.50 as a main ingredient. It was shown to have high antitumor activity on BDF1 mice transplanted with LLC cells and nude mice transplanted with NCI-H23 cells.

(3) Isolation of SB365 from Fraction SPX3

To isolate an antitumor substance from the fraction SPX3 showing antitumor activity, HPLC was carried out to obtain pure compound, SB365. To identify the structure of SB365, Lieberman-Burchard reaction, IR, $^1$H-NMR, $^{13}$C-NMR, and ethanol/sulfuric acid hydrolysis were carried out. As a result, SB365 was confirmed as hederagenin 3-O-α-L-rhamnopyranosyl(1→2)-[β-D-glucopyranosyl(1→4)]-α-L-arabinopyranoside, which is a saponin ingredient that had already been isolated from Pulsatillae radix.

The Pulsatillae radix extracts according to the present invention or pure SB365 compound isolated therefrom have a weak cytotoxicity against solid tumor cells, but unexpectedly showed excellent antitumor activity in animal experiments. Thus, they can improve problems caused by previous antitumor agents on clinical use, e.g. reducing immune responses due to decreasing blood cells. It is also anticipated that they show low toxicity on rapidly dividing cells like hematopoietic cells, etc.

The Pulsatillae radix fractions and SB365 according to the present invention may be combined with pharmaceutically acceptable carriers that are conventionally used, and manufactured into various formulations that are conventional in the pharmaceutical field, for example, orally administrable formulations like solutions, suspensions, etc.; injectable formulations like injectable solution or suspension, ready-to-use injectable dry powder, etc.; and topically administrable formulations like ointments, creams, and solutions. Particularly, the active ingredient of the present invention is soluble in water, and may be dissolved in various solutions such as physiological saline, Ringer's solution, and nutrient solution, etc. Such pharmaceutical formulations may be intravenously, subcutaneously, intraperitoneally, or topically administered.

A recommended dosage of the active ingredient of the present invention to human beings is 3.5~8.0 mg/kg body weight in case of SB365, 20~40 mg/kg body weight in case of fraction SPX3, or 200~300 mg/kg in case of fraction WT. The optimal dosage is 6.5 mg/kg body weight in case of SB365, 25 mg/kg body weight in case of fraction SPX3, or 250 mg/kg body weight in case of fraction WT. However, such dosage may be appropriately adjusted depending on age, body weight, health, severity of disease of patients.

BEST MODE FOR CARRYING OUT THE INVENTION

This invention will be better understood from the following examples. One skilled in the art will readily appreciate the specific materials and results described are merely illustrative of, and are not intended to, nor should be intended to, limit the invention as described more fully in the claims, which follow thereafter.

Example 1

Preparation of Fraction Wt

Figure 1:
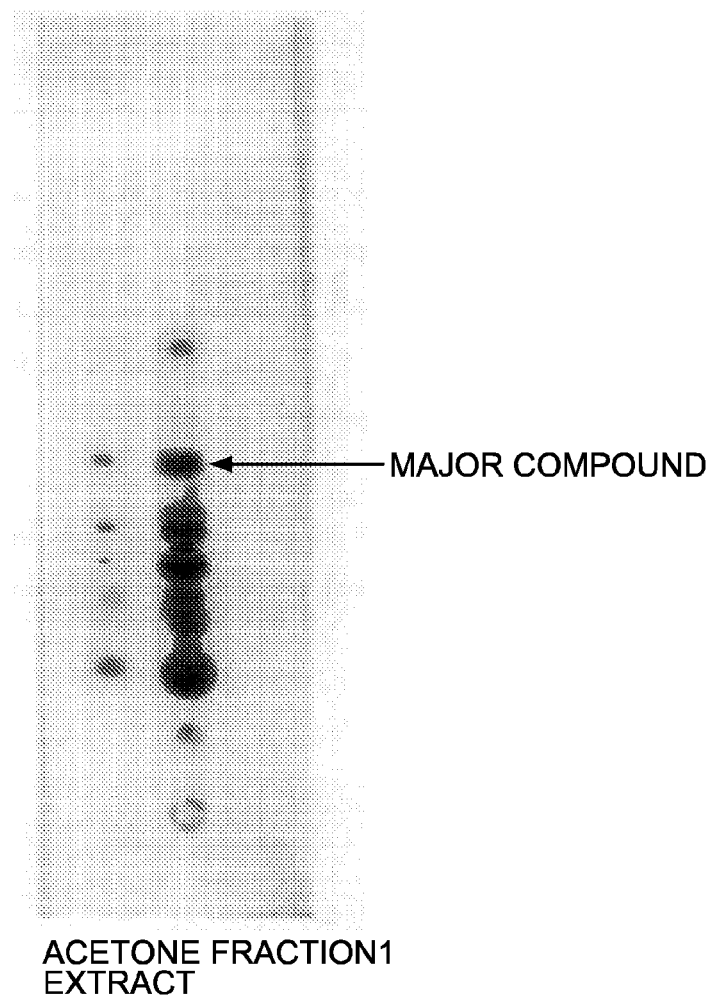
FIG. 1 shows silica gel TLC patterns of fraction WT.

Pulsatillae radix powder of 50 g was extracted three times with 500 ml of 50% aqueous solution of ethanol, and the extract was dried under reduced pressure to obtain 22 g of dried materials. To this dried materials was added 300 ml of acetone, and the mixture was shaken and centrifuged at 3,000 rpm. The supernatant was removed therefrom to give a precipitate. For this precipitate, the acetone treatment was repeated twice. The acetone layer was discarded, and an insoluble part was dried to obtain 17.8 g of dried materials (fraction WT). The obtained fraction WT was subjected to silica gel TLC (developing solvent: butanol:acetic acid:water in the ratio of 4:1:1, color reaction: sulfuric acid-spraying followed by heating). The result is shown in FIG. 1. In FIG. 1, a blue spot having the $R_f$ in the range of 0.48 to 0.50 corresponds to the active ingredient of the present invention as described below. As shown in Experimental Example 1 below, fraction WT showed relatively high antitumor activity (inhibition rate of tumor growth: 57%) on BDF1 mice transplanted with LLC cells.

Example 2

Preparation of Fractions SPX

Figure 2:
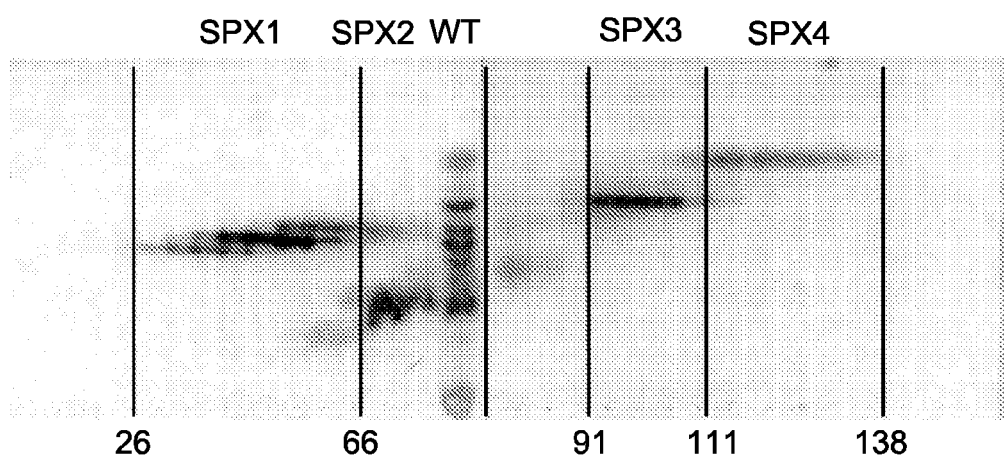
FIG. 2 shows silica gel TLC patterns of fraction SPX3 purified on a Sephadex LH20 column.

Fraction WT of 560 mg was further fractionated on Sephadex LH20 column (200 g, 60×4 cm) using a mixed solution of methanol and water (80:20) with the flow rate of 1 ml/min, and the fraction volume of 0.5 ml/tube. These fractions were spotted on a silica gel thin layer in order, and developed to obtain factions (developing solvent: butanol: acetic acid:water in the ratio of 4:1:1, color reaction: sulfuric acid-spraying followed by heating). The result is shown in FIG. 2. In FIG. 2, SPX1 (139 mg, 24.8%) was obtained by collecting test tube numbers 26 to 66, and consisted of 4 major spots, lower one of which developed yellow color upon reacting with sulfuric acid. SPX2 (344 mg, 61.4%) was obtained by collecting test tube numbers 66 to 91, and consisted of 2 major spots. SPX3 (61 mg, 10.9%) was obtained by collecting test tube numbers 91 to 111, and developed red color at first, and then blue color with the lapse of time, upon spraying sulfuric acid followed by heating. Fraction SPX3 contained a spot having the $R_f$ value in the range of 0.48 to 0.50 as its major ingredient. SPX4 (15.7 mg, 2.8%) was obtained by collecting test tube numbers 111 to 138. Fractions SPX3 and SPX4 had relatively high purity showing one spot on the thin layer.

As shown in Experimental Example 1 below, SPX3 exhibited 60% of the inhibition rate of tumor growth on 15 days from its administration. By contrast, SPX1, SPX2, and SPX4 did not exhibit any action, and so it could be assumed that the substance developing blue color against sulfuric acid was an ingredient with antitumor activity. This SPX3 fraction may be used as an antitumor agent in itself.

Example 3

Isolation of SB365

In order to isolate a pure substance from fraction SPX3, HPLC was carried out as follows.

Figure 3:
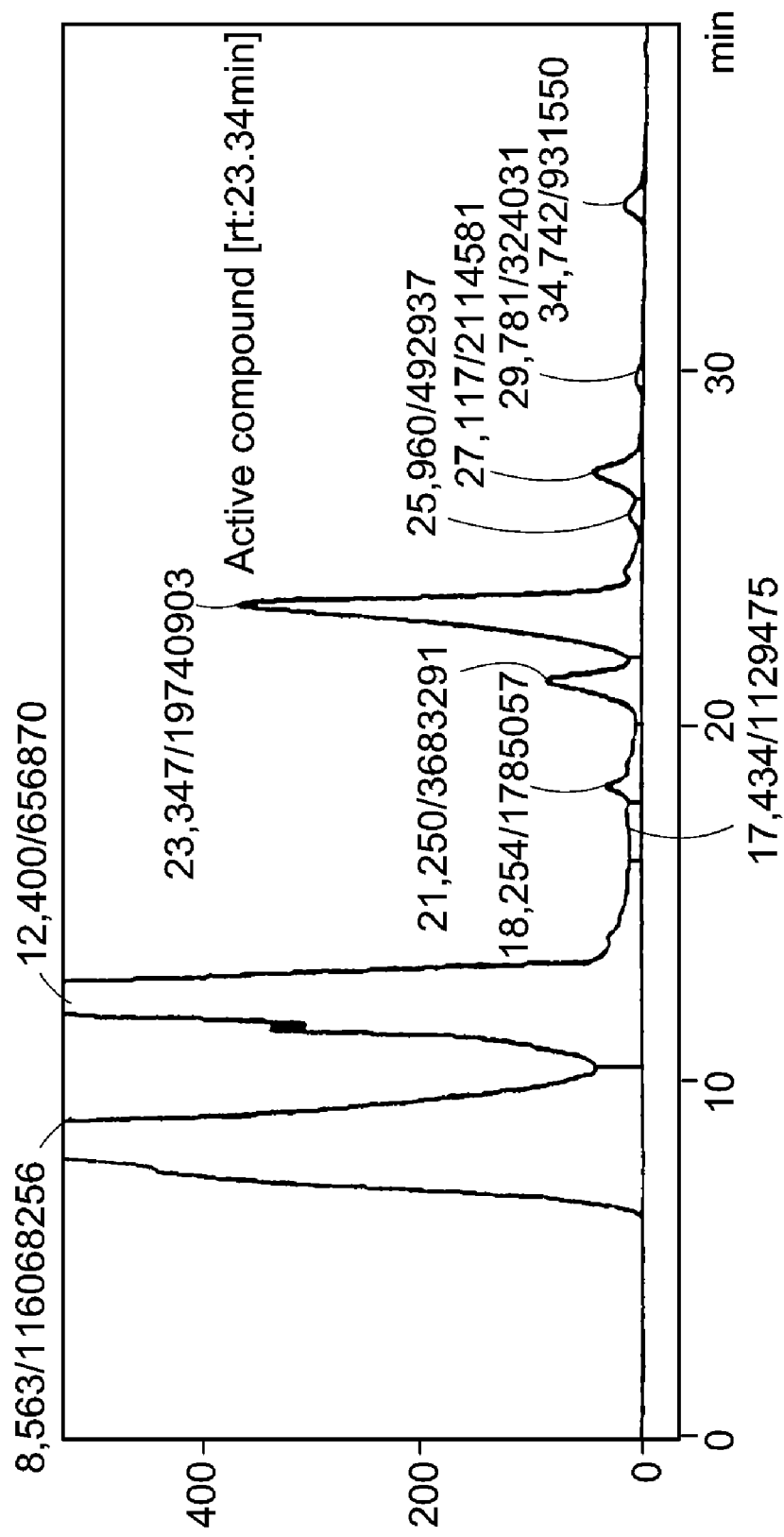
FIG. 3 is an HPLC chromatogram of fraction SPX3; and,
FIG. 4 is an HPLC chromatogram of SB365.
Figure 4:
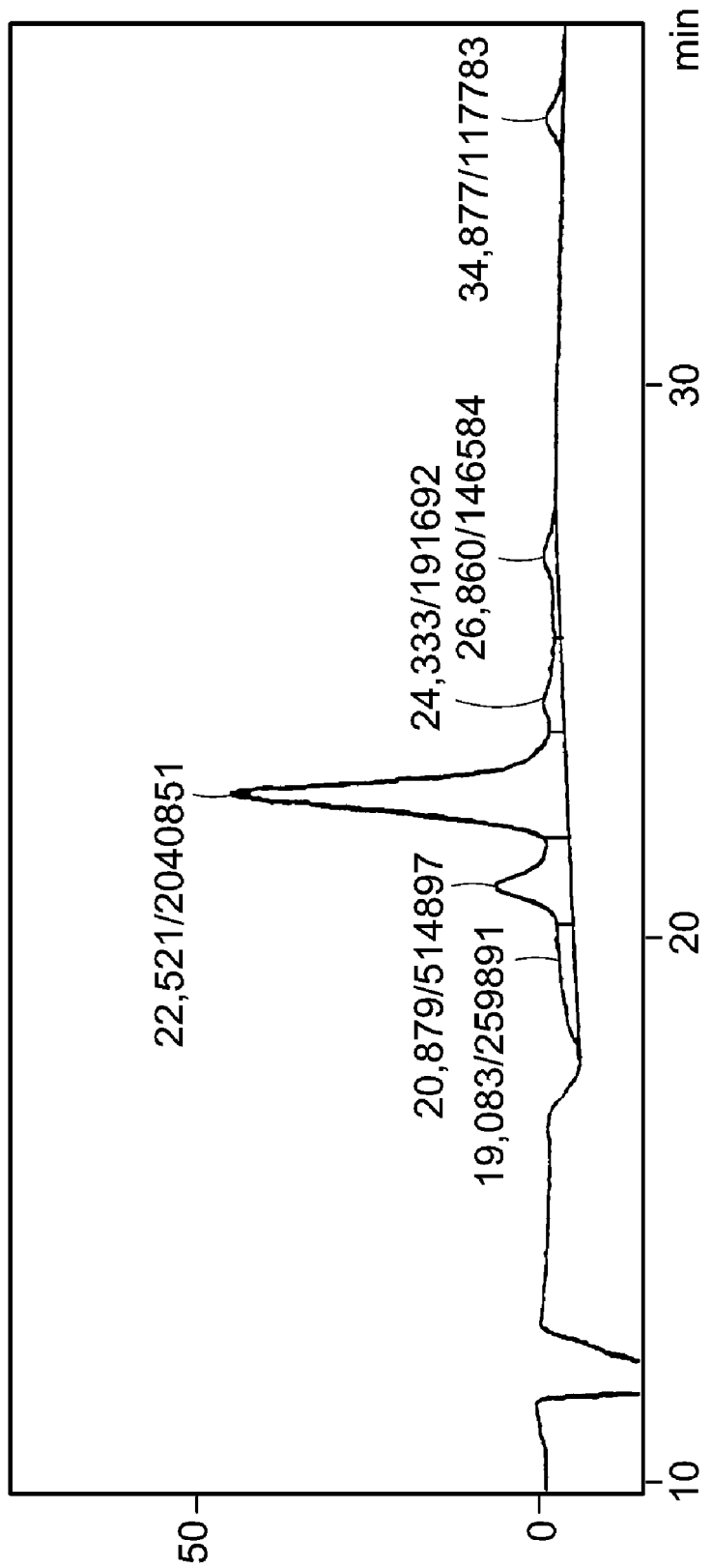

Reverse-phased silica gel (RP-$C_{18}$, 250×10 mm, manufactured by Metachem) was used as the fixed phase, and a mixed solution of methanol and water (80:20) was used as the mobile phase. The detection wavelength was 210 nm, and the flow rate was 1 ml/min. The result is shown in FIG. 3. As shown in FIG. 3, SPX3 consisted of 3 major substances. From the obtained fractionated amounts, peaks at $R_t$ of 8.5 min and 10.4 min contained small amounts of ingredients, and a peak at $R_t$ of 23.3 min contained the major ingredient. Thus, it was assumed that the latter would have antitumor activity. As described above, the substance with $R_t$ of 23.3 min that developed blue color with sulfuric acid and would be the active ingredient was collected to obtain SB365 of 2.8 mg from 31 mg of SPX3. The collected fraction at $R_t$ of 23.3 min was dried, and was subjected to HPLC under the condition as described above to measure its purity. The result is shown in FIG. 4. From FIG. 4, it was confirmed that SB365 was a pure substance. The obtained SB365 was directly used for the structural identification and antitumor activity test below.

As shown in Experimental Examples 1 and 2 below, SB365 exhibited 81% and 82.1% of the inhibition rate of tumor growth on BDF1 mice transplanted with LLC cells and nude mice transplanted with NCI-H23 cells, respectively, which could be said to be excellent antitumor activities.

Example 4

Structural Identification and Confirmation of the Active Compound Sb365

SB365 isolated in the above was the white amorphous form with m.p. 239~241° C. and $[\alpha]_D$+23.6° (c, 0.2, MeOH), and was positive in Liebermann-Buchard reaction, and so confirmed as a glycoside. In addition, according to IR ($cm^{-1}$), peaks were observed at 3400 (br, —OH), 2940 (br, C—H), 1695 (C=O), 1455, and 1040 (C=O). It was also assumed as a glycoside from the absorption peaks in the ranges of 1000-1100 and 3000-3400.

In view of $^1$H-NMR, it had NMR patterns typical of saponins. Six —$CH_3$ groups were observed at 0.91, 0.92, 0.98, 1.00, 1.07, and 1.21 ppm, and another —$CH_3$ group was observed as doublet at 1.64 ppm. It could be seen from this that the compound comprised one rhamnose group in its sugar groups. Anomeric protons were observed at 6.25 (br.), 5.11 (1H, J=7.80 Hz), and 4.97 ppm (1H, J=6.66 Hz). Therefore, SB365 was confirmed as a glycoside having three sugar groups.

According to $^{13}$C-NMR, a hydroxymethyl group was observed at 65. 4 ppm (C-23), and three anomeric carbon signals was observed at 104.2 (C-1'), 106.7 (C-1'''), and 101.7 ppm (C-1''). Two olefinic carbons were observed at 122.5 ppm (C-12) and 144.8 ppm (C-13), and one carboxy carbon was observed at 180.2 ppm (C-28). In general, about 4 Hz of glycosylation upfield shift is shown when sugar is bound at the 28 position (180.2 ppm→176.2 ppm). In the present compound, the above phenomenon was not observed, and so it was confirmed that the compound does not have a sugar group in the 28 position.

Subsequently, the compound was hydrolyzed in ethanol/sulfuric acid to identify its sugar groups and the structure of aglycone. SB365 was confirmed as hederagenin after comparing physicochemical data of the hydrolysis product, aglycone, $^{13}$C-NMR, and $^1$H-NMR data. Further, the hydrolyzed sugars were confirmed as rhamnose, arabinose, and glucose by comparative TLC.

On the basis of the above analysis results and data in published literatures, SB365 was confirmed as hederagenin 3-O-α-L-rhamnopyranosyl((1→2)-[β-D-glucopyranosyl (1→4)]-α-arabinopyranoside.

$^1$H-NMR and $^{13}$C-NMR data of SB365 are as shown in the following Table 1.

TABLE 1

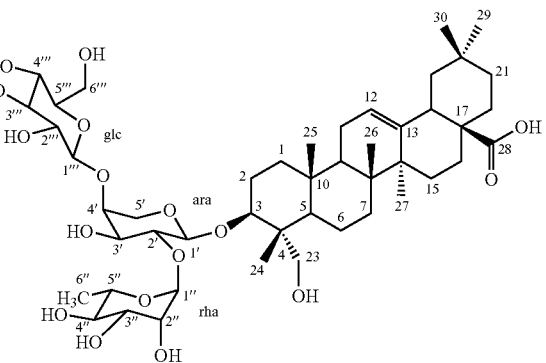

| Position | $^1$H (ppm) | J (Hz) | $^{13}$C (ppm) |
| --- | --- | --- | --- |
| C-1 | | | 38.9 |
| C-2 | | | 26.1 |
| C-3 | 3.28 d | 10.9 | 81.0 |
| C-4 | | | 43.5 |
| C-5 | | | 48.1 |
| C-6 | | | 18.1 |
| C-7 | | | 32.8 |
| C-8 | | | 39.7 |
| C-9 | | | 47.8 |
| C-10 | | | 36.9 |
| C-11 | | | 23.9 |
| C-12 | 5.45 s | | 122.5 |
| C-13 | | | 144.8 |
| C-14 | | | 42.1 |
| C-15 | | | 28.3 |
| C-16 | | | 23.8 |
| C-17 | | | 46.2 |
| C-18 | | | 41.9 |
| C-19 | | | 46.4 |
| C-20 | | | 30.9 |
| C-21 | | | 34.2 |

TABLE 1-continued

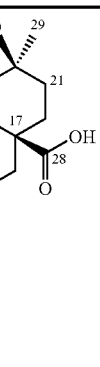

| Position | $^1$H (ppm) | J (Hz) | $^{13}$C (ppm) |
|---|---|---|---|
| C-22 | | | 33.2 |
| C-23 | 4.36, 3.67 | overlap | 65.4 |
| C-24 | 1.07 s | | 14.0 |
| C-25 | 0.91 s | | 16.0 |
| C-26 | 0.98 s | | 17.4 |
| C-27 | 1.21 s | | 26.3 |
| C-28 | — | | 180.2 |
| C-29 | 0.92 s | | 32.8 |
| C-30 | 1.00 s | | 23.7 |
| Arabinose | | | |
| C-1' | 4.97 d | 6.66 | 104.2 |
| C-2' | | | 80.4 |
| C-3' | | | 75.4 |
| C-4' | | | 76.2 |
| C-5' | | | 63.9 |
| Rhamnose | | | |
| C-1'' | 6.25 br | | 101.7 |
| C-2'' | | | 72.3 |
| C-3'' | | | 72.4 |
| C-4'' | | | 74.1 |
| C-5'' | | | 69.6 |
| C-6'' | 1.64 | 5.94 | 18.6 |
| Glucose | | | |
| C-1''' | 5.11 d | 7.80 | 106.7 |
| C-2''' | | | 75.0 |
| C-3''' | | | 78.5 |
| C-4''' | | | 71.2 |
| C-5''' | | | 78.8 |
| C-6''' | | | 62.5 |

Experimental Example 1

Antitumor Activity on BDF1 Mice Transplanted with LLC Cells

The mouse species used in this experiment was BDF1, and healthy male mice with the body weight of 18~25 g were used. These animals were supplied with water and foods ad libitum at a place of controlled temperature in the range of 23~24° C., and were bred with an antibiotic-free mouse feed. LLC cells were subcutaneously cultured in C57BL/6 mice for 14 days. A LLC cell-containing tissue was taken and thereto was added sterilized cold physiological saline water (5 ml/g tissue) to prepare a cell suspension. The cell suspension of 0.2 ml was subcutaneously transplanted to the groin region of BDF1 mouse.

From 24 hours after transplantation, the above mice were divided into several groups consisting of 5 mice. Then, samples, fractions WT and SPX fractions, and SB365, were dissolved in physiological saline, and were injected intraperitoneally at each concentration of 280 mg/kg (WT), 70 mg/kg (SPX1), 171 mg/kg (SPX2), 30.5 mg/kg (SPX3), 8.1 mg/kg (SPX4), and 6.4 mg/kg (SB365). To the negative control group was injected only the physiological saline, and to the positive control group was injected adriamycin (0.5 mg/kg). The injection was scheduled from 24 hours after tumor transplantation to administer the samples successively once a day for 7 days, and stopped for one day, and then, was carried out for 6 more consecutive days.

In order to evaluate toxicity of SB365 on mice, experimental mice were weighed twice a week. Antitumor activity was calculated after measuring tumor volume of the control and test groups on 14th and 15th day after sample administration as follows:

Tumor volume (mm$^3$)=length (mm)×width$^2$ (mm$^2$)/2

Inhibition rate of tumor growth (%)=(C-T)×100/C (C: average tumor volume in the control group, T: average tumor volume in the test group)

The result is shown in the following Table 2.

TABLE 2

Inhibition rate of tumor growth (IR, %) of Pulsatillae radix fractions and SB365 on BDF1 mice transplanted with LLC cells

| Fractions or compounds | Number of mice | Inhibition rate of tumor growth (%) | |
|---|---|---|---|
| | | 14th day$^{a)}$ | 15th day$^{a)}$ |
| WT | 5 | 56 | 55 |
| SPX1 | 5 | 10 | 12 |
| SPX2 | 5 | 25 | 30 |
| SPX3 | 5 | 57 | 60 |
| SPX4 | 5 | 8 | 10 |
| SB365 | 5 | 82 | 79 |
| Adriamycin | 5 | 60 | 64 |

$^{a)}$Days after transplantation of tumor cells

As shown in the above Table 2, fractions WT and SPX3 showed the inhibition rate of tumor growth of 55% and 60%, respectively, and SB365 showed the inhibition rate of tumor growth of 79%, higher than adriamycin of 64% on 15th day from transplantation of tumor cells.

Experimental Example 2

Antitumor Activity on Nude Mice Transplanted with NCI-H23 cells

Female nude mice of the age of 5 weeks weighing 16~25 g obtained from Harlan Co. (USA) were used as experimental animals in this experiment. The mice were used after acclimation for 1 week in an aseptic animal room. The animal room maintained the temperature of 22±2° C., the humidity of 55±5%, and the light and darkness cycle of 12 hours, which was automatically controlled. Solid feed for experimental animals was radiosterilized, and drinking water was sterilized in an autoclave. The animals were supplied with feed and drinking water ad libitum. A human tumor cell line provided by National Cancer Institute (NCI), USA, and preserved in the Korean Research Institute of Bioscience and Biotechnology (KRIBB), Korea, was used. Lung tumor cells, NCI-H23 cells, among the human tumor cells, were transplanted to the nude mice. The tumor cells of 3×10$^7$ cells/ml were subcutaneously transplanted to the mice at a volume of 0.3 ml/20 g body weight. The samples were intraperitoneally injected to the mice every day for 13 days, that is, from 1 day to 14th day except 8th day after tumor cells transplantation. The size of tumor formed during the injection was measured in each animal, and any change in its body weight was also measured. On 16th day after tumor cells transplantation, the nude mice were sacrificed, and the tumor was separated and weighed. To the positive control group was intraperitoneally injected adiamycin of 0.5 mg/kg body weight on 1st, 5th, 9th, and 14th day. The result is shown in the following Table 3.

TABLE 3

Inhibition rate of tumor growth (IR, %) of SB365 on nude mice transplanted with NCI-H23 cells

| Group | Inhibition rate of tumor growth (%) on NCI-H23 | | | | |
|---|---|---|---|---|---|
| | Negative control | Adriamycin (0.5 mg/kg) | SB365 (1.6 mg/kg) | SB365 (3.2 mg/kg) | SB365 (6.4 mg/kg) |
| 16th day[a] | — | 61.5 | 40.1 | 52.3 | 82.1 |

[a]Days after tumor cells transplantation

As shown in the above Table 3, SB365 of 6.4 mg/kg showed a high inhibition rate of tumor growth, 82.1%, on 16th day after tumor cells transplantation.

Experimental Example 3

Cytotoxicity Test

Tumor cells A549, SK-MEL-2, and MCF-7 were obtained from the KRIBB, and used in this experiment. A culture medium was prepared by adding one pack of L-glutamine-containing RPMI1640 medium, 100 ml of fetal bovine serum (FBS) inactivated by heating at a water bath of 50° C. for 30 minutes, 2 g of $NaHCO_3$, 100,000 units of penicillin, and 100 mg of streptomycin, to a sterilized distilled water for injection, adjusting the pH of the mixture with 0.1 N HCl to a total volume of 1 l, and disinfecting the mixture with filtration, and stored at 4° C. before use. The cells were maintained by propagation once every three days, and a solution containing 0.5% trypsin and 2% EDTA in physiological buffered saline (PBS) was used to detach the cells from wells.

Cytotoxicity on tumor cells was measured according to Sulforhodamine-B (SRB) method developed by the NCI in 1989 to measure in vitro antitumor activity of drugs.

Specifically, the cells were detached from wells with 0.5% trypsin-EDTA solution and then, $3\sim5\times10^4$ cells/ml of cell suspension was prepared. Then, the cell suspension (180 µl/well) was added to 96-well plate, and the plate was incubated in an incubator of 37° C., 5% $CO_2$ for 24 hours.

The sample was dissolved in dimethylsulfoxide (DMSO) and diluted with the culture medium or tertiary distilled water to obtain required concentrations for experiment, and serially diluted to a final concentration of DMSO of 0.2% or less. To each well of 96-well plate were added 20 µl of the serially diluted sample solutions, and then, the plate was incubated in an incubator of 37° C., 5% $CO_2$ for 48 hours. At the point of time to add the sample solution, $T_z$ (Time zero) plate was collected. Medium was removed from $T_z$ plate and from each plate after completing the incubation, and to the plates was added 10% trichloroacetic acid (TCA) (50 µl/well). The resulting plates were allowed to stand for 1 hour at 4° C. to immobilize the cells on the bottom of the plates. After completing the cell immobilization, the plates were washed 5~6 times with water to completely remove the remaining TCA solution, and the resulting plates were dried at room temperature to contain no moisture.

To the completely dried plates was added 50 µl of a staining solution with 0.4% SRB in 1% acetic acid to stain the cells for 30 minutes. Then, the plates were washed 5~6 times with 1% acetic acid solution to completely remove SRB unbound to the cells. The plates were dried at room temperature. Thereto was added 100 µl of 10 mM Tris solution to dissolve the dye. Then, OD (optical density) value was measured by microplate reader at a wavelength of 520 nm.

$ED_{50}$ value of the sample on tumor cells [50% effective dose (ng/ml): a concentration at which tumor cell growth is inhibited by 50%] was calculated as follows. $T_z$ value was defined as OD value at the time of starting the incubation after adding the sample, C (control) value as OD value of the well not treated with the sample, and T (test) value as OD value of the well treated with the sample. From the values $T_z$, C, and T, cytotoxicity of the agent was measured by the following formula:

in the case of $T_z \geq T$, $(T-T_z)/(C-T_z)\times100$
in the case of $T_z < T$, $(T-T_z)/T_z\times100$ From the values as calculated above, $ED_{50}$ value of the sample was obtained by using data regression function of Lotus program.

As a result, $ED_{50}$ value of SB365 on human lung tumor cells, A549 cells, human melanoma cells, SK-MEL2, and human breast tumor cells, MCF7 was >20 µg/ml, >10 µg/ml, and >10 µg/ml, respectively. Therefore, SB365 had little cytotoxicity on solid tumor cells.

Formulation Example 1

Preparation of an Injectable Solution Containing Fraction WT

WT fraction of 250 mg obtained in Example 1 was dissolved in 10 ml of physiological saline to prepare an injectable solution.

Formulation Example 2

Preparation of an Injectable Dry Powder Containing Fraction SPX3

SPX 3 fraction of 25 mg obtained in Example 2 was dissolved in 10 ml of Ringer's solution, sterilized and then, freeze-dried to prepare ready-to-use injectable dry powder. This powder would be re-constituted with distilled water for injection before use.

Formulation Example 3

Preparation of an Injectable Solution Containing SB365

SB365 of 6.5 mg obtained in Example 3 was dissolved in 10 ml of Ringer's solution and sterilized to prepare an injectable solution.

INDUSTRIAL APPLICABILITY

Pulsatillae radix factions WT and SPX3, and SB365, hederagenin 3-O-α-L-rhamnopyranosyl ((1→2)-[β-D-glucopyranosyl(1→4)]-α-arabinopyranoside, isolated from the fractions according to the present invention, not only have a high inhibition rate of tumor growth on solid tumor cells, but also can be conveniently used by dissolving in various solutions including physiological saline, Ringer's solution, or nutrient solution because it is readily soluble in water, and has low cytotoxicity enough to ameliorate side effects of previously developed anti-tumor agents. Therefore, it is anticipated to be very useful as a therapeutic agent for solid tumors. In particular, the Pulsatillae radix extract according to the method of the present invention contains high concentration of hederagenin 3-O-α-L-rhamnopyranosyl((1→2)-[β-D-glucopyranosyl (1→4)]-α-L-arabinopyranoside, and so the present invention can provide superior antitumor activity against solid tumors.

What is claimed is:

1. A method of treating solid tumors in a subject in need thereof, comprising administering to the subject a therapeutically effective dose of hederagenin 3-0-α-L-rhamnopyranosyl(1→2)-[β-D-glucopyranosyl(1→4)]-α-L-arabinopyranoside, wherein said hederagenin 3-0-α-L-rhamnopyranosyl (1→2)-[β-D-glucopyranosyl(1→4)]-α-L-arabinopyranoside is contained in a precipitate obtained by extracting Pulsatillae radix with an aqueous solution of ethanol to form a mixture, adding acetone to precipitate the mixture and collecting the precipitate formed.

2. The method according to claim 1, which comprises administering to the subject a therapeutically effective dose of hederagenin 3-0-α-L-rhamnopyranosyl(1→2)-[β-D-glucopyranosyl(1→4)]-α-L-arabinopyranoside by dissolving hederagenin 3-0-α-L-rhamnopyranosyl(1→2)-[β-D-glucopyranosyl(1→4)]-α-L-arabinopyranoside in a solution selected from the group consisting of physiological saline, Ringer's solution, and nutrient solution.

3. The method according to claim 1, wherein the precipitate is administered at a daily dose of 200 to 300 mg/kg body weight.

4. A method of treating solid tumors in a subject in need thereof, comprising administering to the subject a therapeutically effective dose of hederagenin 3-O-α-L-rhamnopyranosyl(1→2)-[β-D-glucopyranosyl(1→4)]-α-L-arabinopyranoside, wherein said hederagenin 3-0-α-L-rhamnopyranosyl (1→2)-[β-D-glucopyranosyl(1→4)]-α-L-arabinopyranoside is contained in a fraction obtained by extracting Pulsatillae radix with an aqueous solution of ethanol to form a mixture, adding acetone to precipitate the mixture, collecting the resultant precipitate, drying the precipitate, reconstituting the precipitate, fractionating the reconstituted precipitate by gel filtration, subjecting the fractions to thin layer chromatography and collecting a fraction which has an Rf value of 0.48 to 0.50.

5. The method according to claim 4, wherein the fraction is administered at a daily dose of 20 to 40 mg/kg body weight.

6. The method of claim 1 or 4, wherein the solid tumors are present in a subject suffering from one or more diseases selected from the group consisting of lung cancer and breast cancer.

* * * * *